(12) United States Patent
Lucena et al.

(10) Patent No.: US 11,107,562 B2
(45) Date of Patent: Aug. 31, 2021

(54) CLUSTERING DATA REGARDING HEALTH CARE PROVIDERS

(71) Applicant: Clover Health, Jersey City, NJ (US)

(72) Inventors: Brian Lucena, Jersey City, NJ (US); Ian Blumenfeld, Jersey City, NJ (US)

(73) Assignee: Clover Health, Jersey City, NJ (US)

( * ) Notice: Subject to any disclaimer, the term of this patent is extended or adjusted under 35 U.S.C. 154(b) by 421 days.

(21) Appl. No.: 16/130,065

(22) Filed: Sep. 13, 2018

(65) Prior Publication Data

US 2020/0090791 A1    Mar. 19, 2020

(51) Int. Cl.
*G16H 10/60* (2018.01)
*G06F 16/28* (2019.01)

(52) U.S. Cl.
CPC .......... *G16H 10/60* (2018.01); *G06F 16/285* (2019.01)

(58) Field of Classification Search
CPC ............................ G16H 10/60; G06F 16/285
USPC ....................................................... 705/2–3
See application file for complete search history.

(56) References Cited

U.S. PATENT DOCUMENTS

| | | | | |
|---|---|---|---|---|
| 7,590,550 B2 * | 9/2009 | Schoenberg | ............ | G06F 16/22 |
| | | | | 705/2 |
| 7,818,183 B2 * | 10/2010 | Schoenberg | ........... | G06Q 10/10 |
| | | | | 705/2 |
| 7,840,418 B2 * | 11/2010 | Schoenberg | ........... | G06Q 10/10 |
| | | | | 705/2 |
| 7,848,937 B2 * | 12/2010 | Schoenberg | ........... | G16H 40/20 |
| | | | | 705/3 |
| 7,890,351 B2 * | 2/2011 | Schoenberg | ....... | G06Q 30/0641 |
| | | | | 705/3 |
| 7,912,737 B2 * | 3/2011 | Schoenberg | ........... | G06Q 40/08 |
| | | | | 705/3 |
| 8,463,620 B2 * | 6/2013 | Schoenberg | ........... | G16H 80/00 |
| | | | | 705/2 |
| 2008/0243539 A1 | 10/2008 | Barish et al. | | |
| 2009/0089074 A1 | 4/2009 | Schoenberg | | |

(Continued)

FOREIGN PATENT DOCUMENTS

AU    2007292359    3/2008

OTHER PUBLICATIONS

PCT Search Report and Written Opinion dated Nov. 27, 2019 for PCT Application No. PCT/US19/51021, 10 pages.

*Primary Examiner* — Michael Tomaszewski
(74) *Attorney, Agent, or Firm* — Lee & Hayes, P.C.

(57) ABSTRACT

Techniques and architectures for clustering health care providers based on data regarding services that have previously been provided by health care providers are described herein. For example, the techniques and architectures may receive data from devices of health care providers regarding services that have been provided by the health care providers to patients. The techniques and architectures may perform various machine learning techniques, including clustering, to categorize health care providers into multiple clusters based on the services that were provided. Health care providers that lie within a cluster may be associated with a category of the cluster. While health care providers that lie outside a cluster, and have designated themselves as being associated with or are otherwise associated with a practice area that is associated with the cluster, may be flagged as potentially practicing outside an area that is designated by or otherwise associated with the health care providers.

20 Claims, 4 Drawing Sheets

(56) References Cited

U.S. PATENT DOCUMENTS

| | | |
|---|---|---|
| 2009/0281831 A1 | 11/2009 | Richards et al. |
| 2014/0129260 A1* | 5/2014 | Kang .................... G16H 20/10 |
| | | 705/3 |
| 2015/0073833 A1* | 3/2015 | Norris .............. G06Q 10/06393 |
| | | 705/3 |
| 2015/0213233 A1* | 7/2015 | Fleming ................ G16H 10/60 |
| | | 705/2 |
| 2016/0048644 A1 | 2/2016 | Anderson et al. |
| 2017/0124266 A1 | 5/2017 | Hasan et al. |

* cited by examiner

CLUSTERING DATA REGARDING HEALTH CARE PROVIDERS

BACKGROUND

Current search algorithms often inaccurately identify doctors or other health care providers that are best suited for a situation. For example, a search engine that analyzes thousands of pieces of data on websites, may spend considerable time and/or computing resources finding results that satisfy input from a user. Since such techniques rely on a search term that is input by the user, the results are limited to a specific set of data that matches the search term. Further, doctors sometimes advertise themselves as being associated with a practice area that is outside of the procedures the doctors actually perform. For example, a doctor may claim to be a primary care physician for business or insurance reasons, but perform very few actions that are generally associated with primary care. This also results in inaccurate search results. As such, even when a variety of computing resources and/or bandwidth are used to identify doctors or other health care providers for a situation, the results are undesirable.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

DETAILED DESCRIPTION

Figure 1:
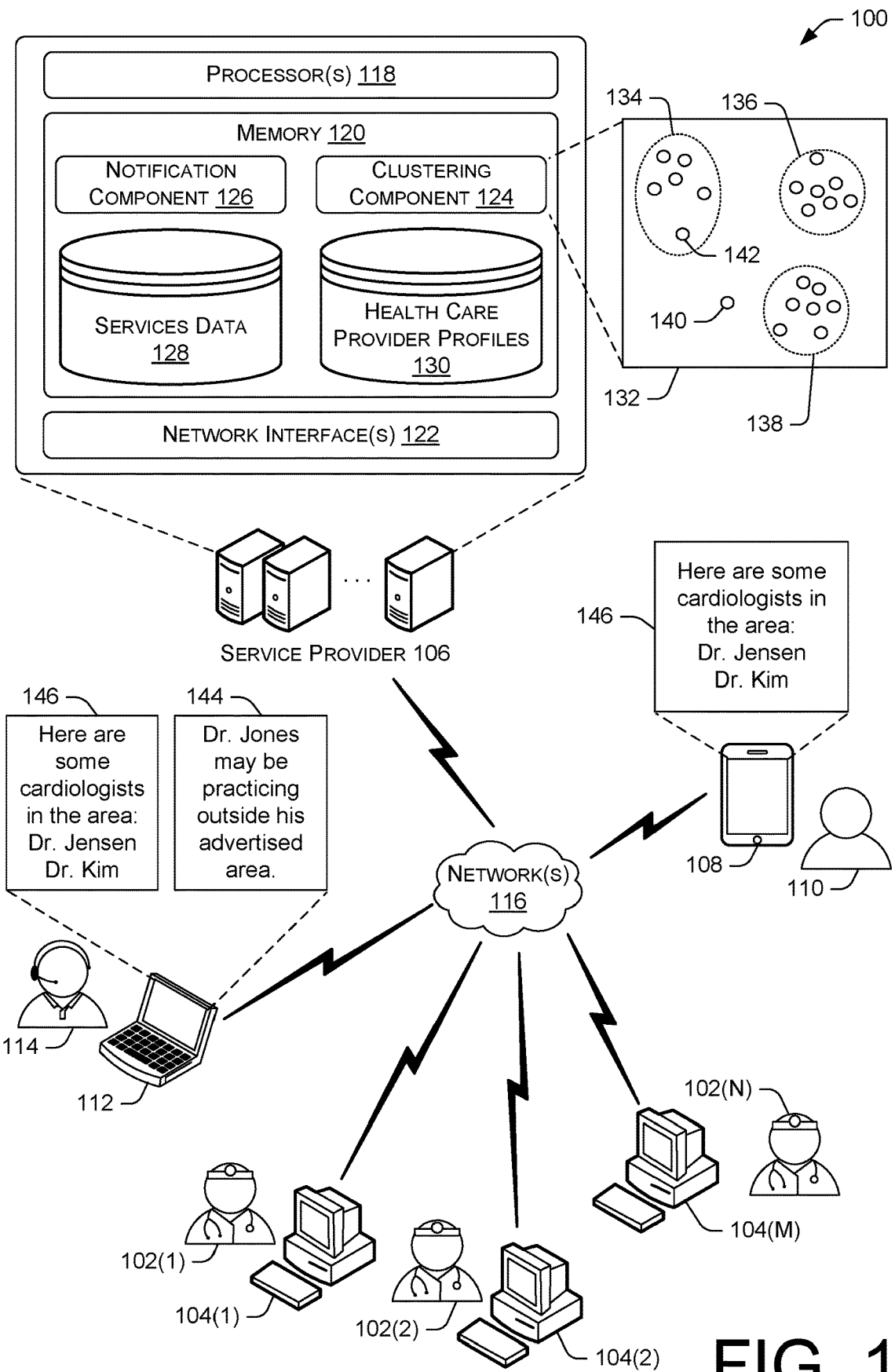
FIG. 1 illustrates an example architecture in which techniques described herein may be implemented.

This disclosure describes, in part, techniques and architectures for clustering health care providers based on data regarding services that have previously been provided by health care providers. For example, the techniques and architectures may receive data from devices of health care providers regarding services that have actually been provided by the health care providers to patients (e.g., during the course of a visit, interaction, etc.). The techniques and architectures may perform various machine learning techniques, including clustering, to categorize health care providers into multiple clusters based on such services that were provided. Health care providers that lie within a cluster may be associated with a category of the cluster. While health care providers that lie outside a cluster, and have designated themselves as being associated with or are otherwise associated with a practice area that is associated with the cluster, may be flagged as potentially practicing outside an area that is designated by or otherwise associated with the health care providers.

Such techniques may assist in accurately identifying health care providers for a situation. For example, the categorization may be used to search through health care providers and obtain more accurate results or recommendations of health care providers, in comparison to previous techniques. Further, the categorization may identify health care providers that potentially practice outside an area that is designated by the health care providers. Ultimately, the techniques and architectures discussed herein may reduce computing resources and/or bandwidth needed to evaluate or search through thousands, hundreds of thousands, or even millions of pieces of data for health care providers. Further, the techniques and architectures may provide useful tools to various entities, such as health care providers, insurance companies, service providers associated with the health care providers, and so on.

As one example, a service provider may receive data from multiple computing devices associated with multiple health care providers. The service provider may operate as a remote computing system that is positioned within a network to receive data from the multiple computing devices that are distributed across a variety of locations. The data may indicate services that have been provided by the health care providers, such as procedures, medical encounter, or other actions that have been performed by a health care provider for a patient. For example, the data may include information describing a visit between a health care provider and a patient.

The service provider may analyze the data to cluster the health care providers. For example, the service provider may determine types of services that have been provided by a health care provider to patients, types of services that have recently been provided by a health care provider to patients, types of services that have been provided most frequently by a health care provider, a number of times a type of service has been provided by a health care provider, a number of times a type of service has been provided by a health care provided to a specific patient, a number of patients that have received a type of service from a health care provider, and so on. Similar determinations may be performed for each of the health care providers. Based on such determinations, the service provider may cluster the health care providers into multiple clusters. For example, health care providers that frequently perform the same types of procedures may be clustered together.

In some examples, the clustering may be used to categorize the health care providers. For example, if a first set of health care providers are clustered together for frequently performing joint replacement surgeries (e.g., each perform more than a threshold number of joint replacement surgeries, joint replacement surgeries are a majority of the services rendered for each health care provider, etc.), the first set of health care providers may be associated with a first category indicating such. Further, if a second set of health care providers are clustered together for frequently delivering babies (e.g., each perform more than a threshold number of deliveries, deliveries are a majority of the services rendered for each health care provider, etc.), the second set of health care providers may be associated with a second category indicating such. In some examples, a profile or account associated with a health care provider may be updated to indicate a category of a cluster with which the health care provider is associated.

Further, in some examples, the clustering may be used to identify a health care provider that may potentially be practicing outside an area that is advertised for the health care provider. For example, the service provider may evaluate a health care provider to see if the health care provider performs services that are claimed to be performed by the health care provider. To illustrate, if the health care provider has designated himself or herself as a primary care physician in a profile or account or the health care provider has otherwise been designated as a primary care physician, the service provider may check to see if the health care provider is within a cluster that is associated with primary care. In some examples, if the health care provider is not associated with the primary care cluster, the service provider may categorize the health care provider as practicing outside a designated area (e.g., flag the health care provider). Additionally, or alternatively, in some examples, if the health care provider is not associated with the primary care cluster, the service provider may send a notification to an entity, such as an insurance company, employer, the health care provider, etc. The notification may alert the entity of the situation. The entity may then evaluate the health care provider or perform a variety of other actions.

In some examples, the service provider may use categories associated with health care providers to provide data regarding the health care providers. For example, the service provider may receive a request for a recommendation of a health care provider that is associated with a particular category. The request may be received from any number of devices, such as a device of a potential patient, a device of an insurance company, a device of a customer service representative for a hospital or insurance company, etc. In response, the service provider may identify one or more health care providers that are associated with the particular category and provide information about the one or more health care providers. The information may include contact information for the one or more health care providers, a description of the one or more health care providers, hours of operation for the one or more health care providers, information to schedule an appointment with the one or more health care providers (e.g., a calendar, link to make an appointment, etc.), or any other information. By using categories that are determined for services that have actually been performed by health care providers, the service provider may provide accurate information as a response.

In some examples, the techniques discussed herein may be implemented to prevent fraud (e.g., flagging a health care provider that lies outside an advertised practice area so that information about the health care provider may be updated, users may be notified of the situation, etc.).

This brief introduction is provided for the reader's convenience and is not intended to limit the scope of the claims, nor the proceeding sections. Furthermore, the techniques described in detail herein may be implemented in a number of ways and in a number of contexts. Some example implementations and contexts are provided with reference to the following figures, as described below in more detail. It is to be appreciated, however, that the following implementations and contexts are but some of many.

Example Architecture

FIG. 1 illustrates an example architecture 100 in which in which techniques described herein may be implemented. The architecture 100 includes a plurality of health care providers 102(1)-102(N) (collectively referred to as "the health care providers 102") that are associated with a plurality of computing devices 104(1)-104(M) (collectively referred to as "the computing devices 104"), respectively. N and M may each represent a number greater than 1 and may be the same or different numbers. In some examples, the computing devices 104 are associated with one or more hospitals, while in other examples the computing devices 104 may be associated with other facilities or locations. The architecture 100 also includes a service provider 106 (sometimes referred to as a remote computing system) that may facilitate various functionality discussed herein. For example, the service provider 106 may receive data from the computing devices 104 regarding services that have been performed by the health care providers 102. The service provider 106 may analyze the data to cluster and/or categorize the health care providers 102. The service provider 106 may use the clusters and/or categorization to provide information to a user device 108 associated with a user 110, a medical service device 112 associated with a user 114, or perform other processing. The computing devices 104, the service provider 106, the user device 108, and/or the medical service device 112 may communicate via one or more networks 116. The one or more networks 116 may include any one or combination of multiple different types of networks, such as cellular networks, wireless networks, Local Area Networks (LANs), Wide Area Networks (WANs), the Internet, and so on.

Each of the health care providers 102 (sometimes referred to as a practitioner) may be any individual who provides healthcare services. For example, a health care provider may be a doctor of medicine or osteopathy, optometrist, nurse practitioner, chiropractor, dentist, phycologist, optometrist, physical therapist, physician assistant, etc. In some examples, a health care provider is defined by a law or agency, such as by state or federal law. In other examples, a health care provider is not defined by a law or agency. Further, although many examples discussed herein refer to health care providers, in other examples the health care providers may be any type of individual that provides a service.

In the example architecture 100, each of the health care providers 102 provides services to patients. The services may include a procedure (e.g., surgery, medical test, treatment, etc.), medical or clinical encounter (e.g., check-up, physical, etc.), or any other act to diagnose, treat, improve health, or otherwise assist a patient. The services may be provided in-person (e.g., a doctor is physically present with a patient at the doctor's office, the patient's home, a temporary location, etc.), over a communication channel (e.g., telephone, video conference, email, text message, social media service, etc.), through a virtual environment (e.g., virtual reality, augmented reality, etc.), etc. In many examples, services provided by a health care provider may include services that are directed by the health care provider and/or performed by assistants or others associated with the health care provider, such as a blood test that is authorized by a doctor and given by an assistant, medical imaging that is authorized by a doctor and taken by a radiology technician, etc.

The health care providers 102 (or others associated with the health care provider 102) may report information regarding services that are performed by the health care providers 102. The information may be input into the computing devices 104 to generate data. In one illustration, the health care provider 102(1) (or an assistant) may use the computing device 102(1) to fill-out a digital form regarding a visit or procedure that has been performed by a doctor. In another illustration, the health care provider 102(1) (or an assistant) may fill-out a paper form that is then scanned into the computing device 104(1) to generate data regarding a service provided.

Additionally, or alternatively, in some examples, the computing devices 104 may generate data automatically regarding services that are performed by the health care providers 102. In one illustration, the computing device 104(1) may be implemented as, or be associated with, a medical device that captures or otherwise generates data regarding a patient (e.g., an electronic medical device configured to capture digital data). Such data may be associated with the patient and/or the health care provider 102(1). In another illustration, the computing device 104(1) may include a camera, microphone, or other device to capture images, audio, etc. for the health care provider 102(1) regarding services performed by the health care provider 102(1) (e.g., the health care provider 102(1) may wear a wearable device that monitors activities performed by the health care provider 102(1)). In some instances, images, audio, or other captured data may be analyzed at the computing device 104(1) and/or the service provider 106. For example, image analysis including computer vision and/or image processing may be performed to determine actions that are performed by the health care provider 102(1) (e.g., images captured by a camera and/or audio captured by a microphone in an operating room may be analyzed to determine a type of surgery that was performed).

Additionally, or alternatively, in some examples, the computing devices 104 may implement a virtual assistant that generates data regarding services that are performed by the health care providers 102. A virtual assistant (sometimes referred to as an intelligent personal assistant) may assist a health care provider in diagnosing a patient, storing data about a patient (e.g., in a medical record), treating a patient, performing a procedure, etc. A virtual assistant may communicate with a health care provider in a variety of manners, such as through speech, text, touch, gestures, etc. In some examples, a virtual assistant may have a conversation with a health care provider and/or patient. A virtual assistant may utilize speech recognition and/or Natural Language Processing (NLP) techniques.

Data regarding a service provided by one or more of the health care providers 102 may include a variety of information. For example, the data may indicate a name of a patient, social security number or other identifying information for a patient, date of birth of a patient, address of a patient, location where a service was rendered, identifier of a health care provider that provided the service (e.g., a name, number, etc. of a doctor), a type of service provided (e.g., a medical code or value associated with a service), a description of a service provided (e.g., notes, comments, etc.), billing instructions, insurance information for a patient (e.g., identifying an insurance company to bill a visit to), images for a service provided (e.g., still images, videos, medical imaging images, etc.), audio for a service provided, data from a medical device (e.g., data from an electronic medical device), etc. In some instances, the data is formatted and/or provided according to a particular standard, such as Current Procedural (CPT) codes, International Statistical Classification of Diseases and Related Health Problems (ICD) classifications, and so on. Further, in some instances, the data is formatted for and/or used by insurance companies, hospitals, etc. Moreover, in some examples, the data is part of a medical record.

The computing devices 104 may send data regarding services that have been provided by the health care providers 102 to the service provider 106. Although the data may also be stored locally at the computing devices 104 and/or sent to other devices, such as the medical service device 112, the user device 108, etc. The data may be provided to the service provider 106 as services are provided by the health care providers 102 (e.g., upon the information being enter, after a visit, etc.), periodically (e.g., in a batched manner once a day, week, month, etc.), and so on. In some examples, the data is provided in a secure manner, such as encrypting the data, sending the data over a secure communication channel (e.g., Virtual Private Network (VPN), communication channel that is established after authenticating, etc.), and so on.

In the example architecture 100, the service provider 106 may be implemented as one or more computing devices, such as one or more desktop computers, laptop computers, servers, and the like. The one or more computing devices may be configured in a cluster, data center, cloud computing environment, or a combination thereof. In one example, the one or more computing devices provide cloud computing resources, including computational resources, network resources, storage resources, and the like, that operate remotely to the computing devices 104. To illustrate, the service provider 106 may implement a cloud computing platform/infrastructure for building, deploying, and/or managing applications and/or services.

As illustrated, the service provider 106 includes one or more processors 118, memory 120, and one or more network interfaces 122. The one or more processors 118 may include a central processing unit (CPU), a graphics processing unit (GPU), a microprocessor, a digital signal processor, and so on. The one or more network interfaces 122 may receive and/or send information over the one or more networks 116 to any device in the architecture 100. For example, the service provider 106 may receive data regarding services that have been provided by the health care providers 102 via the one or more network interfaces 122. As illustrated, the memory 120 may store a clustering component 124, a notification component 126, services data 128, and health care provider profiles 130.

In some examples, the service provider 106 may sanitize data and store the data at the service provider 106. For example, the service provider 106 may sanitize data (received from the computing devices 104) regarding services that have been provided by the health care providers 102 by removing (or anonymizing) personal data. The personal data may include data indicating a name of a patient, social security number or other identifying information for a patient, date of birth of a patient, address of a patient, or any other information that may identify an individual. The sanitized data may be stored as the services data 128 in a database, as illustrated. In other examples, the service provider 106 may store data regarding services that have been provided by the health care providers 102 as the services data 128 without sanitizing the data. In some examples, by sanitizing data and storing such sanitized data, this may secure the data, so that personal data is not available to unauthorized parties in the event that the unauthorized parties gain access to the data. Further, in some examples, such sanitizing may remove the need for the service provider 106 to comply with certain security measures that are associated with personal data (e.g., avoid using encryption, avoid using certain hardware security devices, etc. that may be required for storing personal data).

The clustering component 124 may analyze the services data 128 to cluster the health care providers 102. For example, the service provider 106 may analyze the services data 128 to determine types of services that have been provided by a health care provider to patients, types of services that have recently been provided by a health care provider to patients (e.g., over the last week, month, year, etc.), types of services that have been provided most frequently by a health care provider (e.g., a type of service that the health care provider performs the most, second most, etc.), a number of times a type of service has been provided by a health care provider, a number of times a type of service has been provided by a health care provided to a specific patient, a number of patients that have received a type of service from a health care provider, and so on. The clustering component 124 may generally seek to cluster (sometimes referred to as group) health care providers based on a similarity of the health care providers. For example, health care providers in same cluster (sometimes referred to as a group) are more similar to each other than the health care provider are to health care providers in other clusters. In some examples, the clustering component 124 may use a medical code or value from the service data 128 to cluster the health care providers 102. Further, in some examples, another identifier in the service data 128 may be used to cluster the health care providers 102. Moreover, in some examples, a description in the services data 128 may be used to cluster the health care providers 102. For instance, Natural Langue Processing (NLP) may be performed on a description of services rendered to figure out a type of service that was provided. Furthermore, in some examples, data in the services data 128 from a medical device may be used (e.g., raw or processed data). Further, in some examples, other information from the services data 128 may be used to cluster the health care providers 102.

In one illustration, the clustering component 124 may analyze the services data 128 and cluster multiple health care providers together that each frequently perform knee replacement surgeries. For example, in this illustration, the clustering component 124 may determine that more than 60% of services performed by a first health care provider are knee replacement surgeries. The clustering component 124 may also determine that more than 60% of services performed by a second health care provider are knee replacement surgeries. As such, the first health care provider and the second health care provider may be clustered into the same cluster, along with any other health care providers where knee replacements make up more than more than 60% of their services.

In another illustration, the clustering component 124 may analyze the services data 128 and cluster multiple health care providers together that each perform more than a threshold number of knee replacement surgeries. For example, the clustering component 124 may determine (or reference) an average number of knee replacement surgeries that are performed a year by joint replacement surgeons. The clustering component 124 may cluster together any health care providers that perform at least the average number of knee replacement surgeries.

In yet another illustration, the clustering component 124 may analyze the services data 128 and cluster multiple health care providers together that have each recently performed a certain type of service. For example, the clustering component 124 may determine that each of the multiple health care providers have performed more than a threshold number of knee replacement surgeries over the last year, determine that knee replacement surgeries are in the top three services performed for each of the multiple health care providers, etc.

In some examples, the clustering component 124 may analyze the services data 128 for a relatively large number of health care providers, such as data for all health care providers for which the service provider 106 has received data, data for hundreds or thousands of health care providers, etc. In other examples, the clustering component 124 may analyze the service data 128 for any number of health care providers.

In the example of FIG. 1, a visual representation 132 illustrates one example of clustering health care providers. Here, each node represents a health care provider. Each node may be positioned based on types of services rendered by the health care provider, so that similar health care providers (based on a similarity in services) are positioned closer together. Nodes that are relatively close to each other are referred to as clusters. For example, the visual representation 132 includes three clusters 134, 136, and 138.

In many examples, the clustering component 124 may perform machine learning, such as clustering. Although clustering is discussed in many examples, the service provider 106 may use a variety of machine learning techniques.

In some examples, clustering may result in health care providers positioned at one or more distances from one or more clusters. For instance, a health care provider that has been clustered may be a distance from a center of a cluster. A distance of a health care provider to a center of a cluster may represent a similarity of the health care provider to the cluster. In some examples, a distance of a health care provider to a center of one or more clusters may be associated with the health care provider (e.g., stored in association with the health care provider). In some examples, if a health care provider is positioned relatively close to two or more clusters (e.g., within a particular distance), this may indicate that the health care provider may be practicing in two or more areas which may be an emerging field (e.g. a new specialty).

In some examples, the clustering component 124 may cluster the health care providers 102 and use such clustering to categorize the health care providers 102. For example, the clustering component 124 may determine one or more types of services that are provided by health care providers in a same cluster. To illustrate, if knee replacement surgery is the top service provided by the health care providers in a cluster, the health care providers may be associated with a category of surgeon, joint replacement surgeon, knee replacement surgeon, etc. The category that is selected may vary in breadth depending on how the clustering component 124 is configured (e.g., an administrator indicates to use more detailed or broader categories), how the clusters are organized, and so on. In some examples, the clustering component 124 may categorize a health care provider in a cluster into multiple categories. To illustrate, if knee replacement surgery is the top service provided by health care providers in a cluster and hip surgery is the second, the health care providers may be categorized as both knee replacement surgeons and hip replacement surgeons. Further, in some examples, any number of top services associated with a cluster may be used to categorize health care providers associated with the cluster into one or more categories. In some examples, the clustering component 124 may update a profile or account associated with a health care provider, such as by updating a profile in the health care provider profiles 130 to indicate a category that is being applied to the health care provider. In some examples, each health care provider that has been subjected to clustering processing may be clustered into a cluster (e.g., associated with a nearest cluster) and/or categorized into a category associated with the cluster.

In some examples, the clustering component 124 may determine that a health care provider lies outside a cluster. In one example, the clustering component 124 may determine that a health care provider does not perform a type of service that is associated with a cluster. In another example, the clustering component 124 may determine that a number of times a health care provider has performed a service that is associated with a cluster is less than a threshold. To illustrate, if the clustering component 124 determines that health care providers for a cluster associated with knee replacement surgeries have performed, on average, one hundred knee replacements a year, a threshold may be set to fifty. So, a health care provider that performs less than fifty knee replacement surgeries may lie outside the cluster. In yet another example, the clustering component 124 may determine that a health care provider lies outside a cluster if the health care provider is more than a threshold distance from a center of a cluster.

In the example of FIG. 1, a node 140 represents a node that lies outside the cluster 134 and the cluster 138 (as well as the cluster 136). In some examples, a size of a cluster is configurable by a system, application, user, etc. In one illustration, a cluster size may be set relatively large so that a node 142 is within the cluster 134. In another illustration, the cluster size may be set relatively small, so that the node 142 lies outside the cluster 134.

In some examples, a node that lies outside a cluster may refer to a node that is positioned more than a threshold distance from a center of the cluster. For instance, the node 140 may be considered to lie outside the cluster 138 (even if the node 140 is associated with the cluster 138 as a nearest cluster), since the node 140 is positioned more than a threshold distance from a center of the cluster 138.

In some examples, the clustering component 124 may categorize (or otherwise flag) a health care provider that lies outside a cluster. For example, if a health care provider claims to be a pediatrician, but lies outside a pediatrician cluster, the health care provider may be categorized as potentially practicing outside an area that is designed by the health care provider.

In some examples, the clustering component 124 may cluster health care providers, categorize health care providers, and/or identify outlier health care providers based on a number of times a type of service has been provided by a health care provided to a specific patient and/or a number of patients that have received a type of service from a health care provider. In one illustration, if a health care provider has provided a particular type of service to a particular patient multiple times, the multiple performances of the particular type of service for the particular patient may be counted once (or weighted less than other times the particular type of service has been performed for other patients) in order to cluster or categorize the health care provider. In another illustration, if a health care provider lies outside a cluster due to the health care provider performing a same type of service to a particular patient multiple times (or more than a threshold), the health care provider may be associated with the cluster (or may not be flagged as being outside the cluster). Such processing may help accurately cluster, categorize, and/or identify health care providers in situations where, for example, a health care provider may provide a non-routine service for the same patient multiple times (e.g., a patient happens to need a certain treatment many times and the certain treatment is outside what a doctor regularly does).

The notification component 126 may provide a variety of notifications regarding the health care providers 102. In some examples, the notification component 126 provides a notification 144 indicating that a health care provider practices outside a category that is designated for the health care provider. Here, the notification component 126 may compare a category that is designated for the health care provider (e.g., a category that the health care provider has previously indicated that he or she is associated with, a category that any entity has associated with the health care provider, etc.) to a category of a cluster with which the health care provider is associated. In some examples, such comparison may occur when the clustering component 124 clusters the health care provider and determines a category to associate with the health care provider based on such clustering. In the example of FIG. 1, the notification 144 is sent to the medical service device 112, so that the user 114 may evaluate the health care provider to see if an action should be performed, such as telling the health care provider to change a designated category of services, alerting an employer, etc. Although in other examples, the notification 144 may be provided to other devices (e.g., the user device 108, the computing devices 104, etc.). For example, the notification 144 may be provided to one of the computing devices 104 that is associated with the health care provider. This may allow the health care provider to update a designated category.

To illustrate, assume that a health care provider has been designated as a pediatrician in a profile. Such designation may have been made by the health care provider, another person, a system, etc. For example, the health care provider may have logged into an account to update the profile. In another example, the health care provider may have previously practiced as a pediatrician, but no longer does (e.g., the profile for the health care provider has not been updated). In yet another example, the health care provider may have been designated a pediatrician as a resident, and thereafter, specialized in a different area. In any event, the clustering component 124 may cluster the health care provider, along with other health care providers, and determine a category for a cluster associated with the health care provider, as discussed above. In this illustration, the health care provider is associated with a cardiologist cluster and lies outside a cluster for pediatricians. As such, the notification 144 may be sent for the health care provider.

In some examples, the notification component 126 may provide a notification 146 identifying one or more health care providers that satisfy a request (e.g., a recommendation). For example, the service provider 106 may receive a request for a recommendation of a health care provider that is associated with a particular category (e.g., a search or other input for pediatricians, pediatricians within proximity to a user, etc.). The request may be received from the user device 108 (e.g., a potential patient), the computing device 112 (e.g., a customer service representative talking with a potential patient to provide a doctor recommendation, etc.). In response, the notification component 126 may identify one or more health care providers that are associated with the particular category by referencing the health care provider profiles 130 (e.g., identify a category in a profile that is the same as the particular category, identify health care providers that are within a geographical area that is requested, etc.). The notification component 126 may then send the notification 146 indicating one or more health care providers that satisfy the request. In some examples, the request may request information for health care providers that have performed more than a number of services of a particular category and the notification 146 may provide information regarding health care providers that have performed more than the number of services of the particular category.

The notification 146 may include a variety of information, such as contact information for a health care provider, a description of a health care provider, hours of operation for a health care provider, information to schedule an appointment with a health care provider (e.g., a calendar, link to make an appointment, etc.), or any other information. In some examples, the notification 146 may rank health care providers based on a number of services that have been performed in a requested category and/or a distance of a health care provider to a center of a cluster.

In some examples, the notification 146 may include information to alert the user 114 and/or the user 110 that a health care provider listed in the notification 146 has been verified. For example, the service provider 106 may provide a digital certificate, icon, or other information to indicate that the service provider 106 has verified that a health care provider has actually performed services that he or she claims to perform (e.g., is clustered into a same category as that designated by the health care provider). This may provide the user 114 and/or the user 110 with an independent and/or trusted third-party verification.

The clustering component 124 and/or the notification component 126 may represent software and/or hardware. While two components are illustrated as an example for performing various functionality, their functionality and/or similar functionality could be arranged differently (e.g., combined into a fewer number of components, broken into a larger number of components, etc.). In some cases of implementing hardware, any or all of the functions may be implemented (e.g., performed) in whole or in part by hardware logic components. For example, and without limitation, illustrative types of hardware logic components that can be used include Field-programmable Gate Arrays (FP-GAs), Application-specific Integrated Circuits (ASICs), Program-specific Standard Products (ASSPs), System-on-a-chip systems (SOCs), Complex Programmable Logic Devices (CPLDs), etc.

The memory 120 (as well as all other memory described herein) may include one or a combination of computer readable media. Computer readable media includes volatile and non-volatile, removable and non-removable media implemented in any method or technology for storage of information, such as computer readable instructions, data structures, program modules, or other data. Computer readable media includes, but is not limited to, phase change memory (PRAM), static random-access memory (SRAM), dynamic random-access memory (DRAM), other types of random access memory (RANI), read-only memory (ROM), electrically erasable programmable read-only memory (EE-PROM), flash memory or other memory technology, compact disk read-only memory (CD-ROM), digital versatile disks (DVD) or other optical storage, magnetic cassettes, magnetic tape, magnetic disk storage or other magnetic storage devices, or any other non-transitory medium that can be used to store information for access by a computing device. As defined herein, computer readable media does not include communication media, such as modulated data signals and carrier waves. As such, computer readable media is non-transitory media.

Although the services data 128 and the health care provider profiles 130 are illustrated as being stored in the memory 120 of the service provider 106, the services data 128 and the health care provider profiles 130 may alternatively, or additionally, be stored at the computing devices 104, the medical service device 112, the user device 108, and/or elsewhere.

The computing devices 104, the medical service device 112, and/or the user device 108 may comprise any type of computing device that is configured to perform an operation. For example, the computing devices 104, the medical service device 112, and/or the user device 108 may be implemented as a laptop computer, a desktop computer, a server, a smart phone, an electronic reader device, a mobile handset, a personal digital assistant (PDA), a portable navigation device, a portable gaming device, a tablet computer, a wearable computer (e.g., a watch, an optical head-mounted display (OHMD), etc.), a portable media player, a television, a set-top box, a computer system in a car, an appliance, a camera, a robot, a hologram system, a security system, a home-based computer system (e.g., intercom system, home media system, etc.), a projector, an automated teller machine (ATM), a medical device (e.g., electronic medical device configured to generate data, such as an electronic thermometer, medical imaging machine, heart rate monitor, etc.), and so on.

The computing devices 104, the medical service device 112, and/or the user device 108 may be equipped with one or more processors, memory, one or more cameras, one or more displays, one or more microphones, one or more projectors, one or more speakers, and/or one or more sensors. The one or more processors may include a central processing unit (CPU), a graphics processing unit (GPU), a microprocessor, a digital signal processor, and so on. The one or more cameras may include a front facing camera and/or a rear facing camera. The one or more displays may include a touch screen, a Liquid-crystal Display (LCD), a Light-emitting Diode (LED) display, an organic LED display, a plasma display, an electronic paper display, or any other type of technology. The one or more sensors may include an accelerometer, compass, gyroscope, magnetometer, Global Positioning System (GPS), olfactory sensor (e.g., for smell), or another sensor. In some examples, the components of the computing devices 104, the medical service device 112, and/or the user device 108 may be configured to receive user input, such as gesture input (e.g., through the camera), touch input, audio or speech input, and so on, and/or may be configured to output content, such as audio, images, video, and so on. The computing devices 104, the medical service device 112, and/or the user device 108 may receive any type of input from a user, such as audio or speech, text, touch, or gesture input received through a sensor. The computing devices 104, the medical service device 112, and/or the user device 108 may also provide any type of output, such as audio, text, interface items (e.g., icons, buttons, menu elements, etc.), and so on.

In some examples, the medical service device 112 and/or the user 114 may be associated with the service provider 106 and/or the health care providers 104. For example, the medical service device 112 and/or the user 114 may provide customer service support (e.g., for recommendations, insurance questions, etc.), office support (e.g., secretaries, administrators, etc.), management services (e.g., for executives, managers, etc.), etc. for the service provider 106 and/or the health care providers 104. To illustrate, the service provider 106 may be part of an insurance company that manages healthcare, and the medical service device 112 and/or the user 114 may provide customer service support for the insurance company. In some examples, the medical service device 112 and/or the user 114 are at the same location, part of the same organization, etc. as the service provider 106 and/or the health care providers 104. In some examples, the service provider 106, the medical service device 112, and/or the user 114 assist patients with Medicare, private versions of Medicare, or other insurance or programs.

Example Processes

Figure 2:
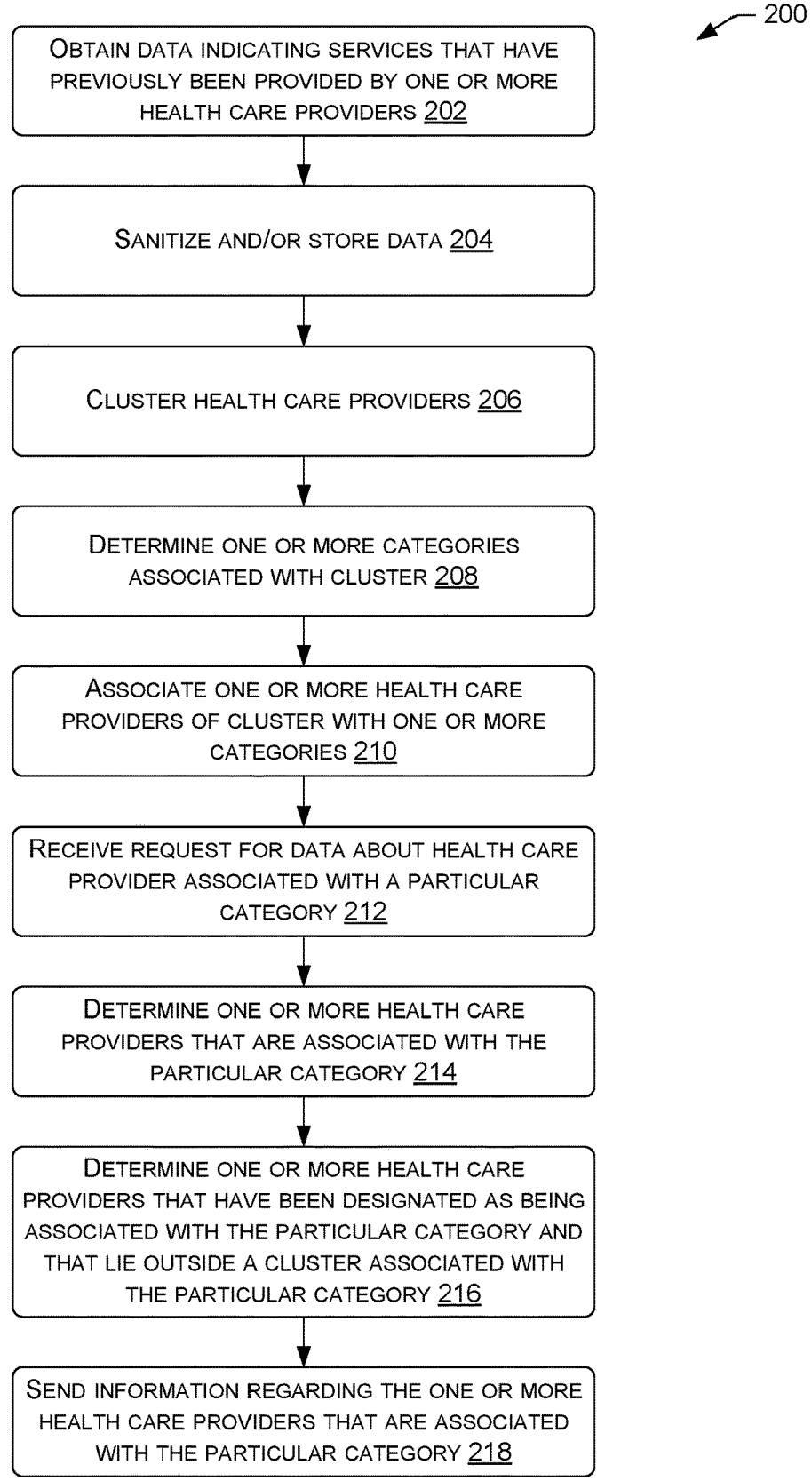
FIG. 2 illustrates an example process for providing information regarding a health care provider(s) that is associated with a category.
Figure 3:
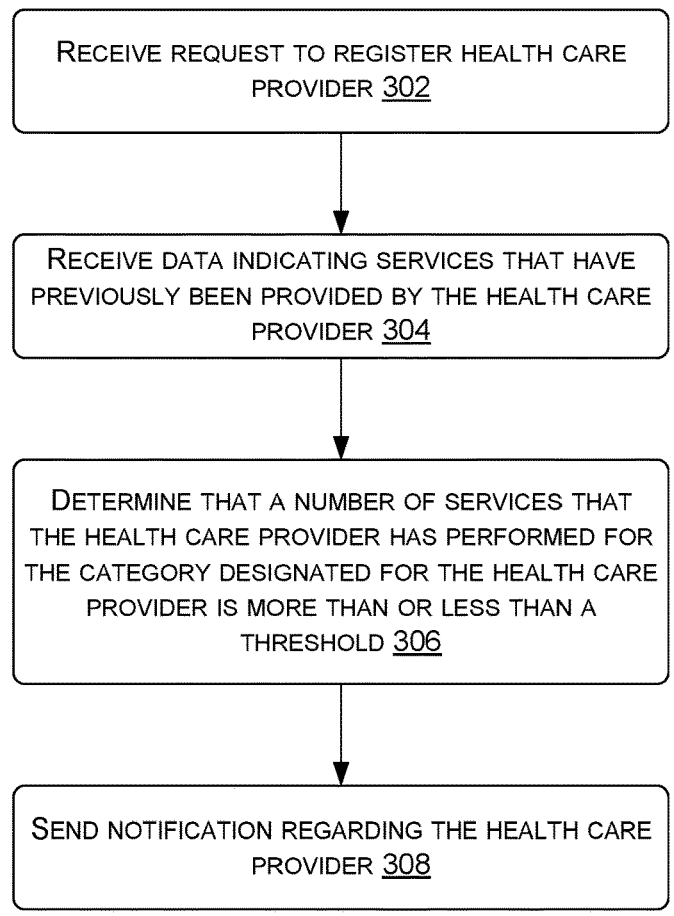
FIG. 3 illustrates an example process for providing information regarding a health care provider that is registering with a system.
Figure 4:
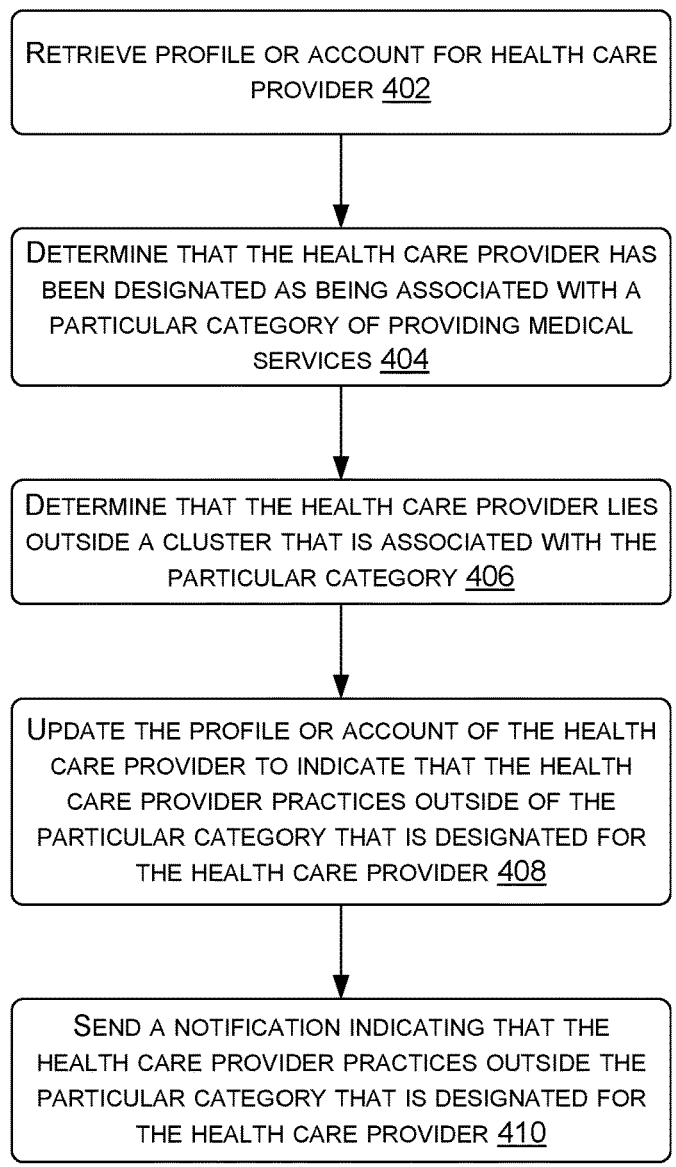
FIG. 4 illustrates an example process for analyzing a category that is designated by a health care provider.

FIGS. 2-4 illustrate example processes 200, 300, and 400 for employing the techniques described herein. For ease of illustration, the processes 200, 300, and 400 will be described as being performed by a computing device. For example, one or more of the individual operations of the processes 200, 300, and 400 may be performed by the service provider 106, the medical service device 112, the user device 108, and/or any other device. However, the processes 200, 300, and 400 may be performed in other architectures. Moreover, the architecture 100 may be used to perform other processes.

The processes 200, 300, and 400 (as well as each process described herein) are illustrated as a logical flow graph, each operation of which represents a sequence of operations that can be implemented in hardware, software, or a combination thereof. In the context of software, the operations represent computer-readable instructions stored on one or more computer-readable storage media that, when executed by one or more processors, perform the recited operations. Generally, computer-readable instructions include routines, programs, objects, components, data structures, and the like that perform particular functions or implement particular abstract data types. The order in which the operations are described is not intended to be construed as a limitation, and any number of the described operations can be combined in any order and/or in parallel to implement the process. Further, any number of the described operations may be omitted.

FIG. 2 illustrates the example process 200 for providing information regarding a health care provider(s) that is associated with a category.

At 202, a computing device may obtain data indicating services that have previously been provided by one or more health care providers. For example, the computing device may receive the data from one or more computing devices that are associated with the one or more health care providers. The data may be received over time (e.g., from various computing devices as the data is generated), at once, and/or in any other manner.

In some examples, at 202, the computing device may receive medical device data (e.g., raw or processed data) from one or more medical devices. In some instances, the medical device data may be received automatically when the one or more medical devices generate the medical device data. The computing device may analyze the medical device data to determine a type of medical device that generated the medical device data. The computing device may then use a machine learning model to infer services that have previously been provided by a health care provider based on the type of medical device that generated the medical device data. Based on the inferring, the computing device may generate data indicating services that have previously been provided by one or more health care providers.

In one example of processing medical device data, the computing device may receive medical device data from a medical imaging machine (e.g., medical images, values, etc. from an X-ray machine). The computing device may analyze the medical device data to determine that the medical device data is in a particular format (e.g., image format, etc.), has particular values (e.g., voltage values, pixels, current values, heart rate values, etc.), identifies a particular machine that generated the medical device data (e.g., a serial number for the medical device, a MAC address for the medical device, etc.), and so on. Based on such determination, the computing device may determine a type of medical device that generated the medical data (e.g., an electronic thermometer, a medical imaging machine, a heart rate monitor, etc.). In some examples, this determination includes using a machine learning model that has learned what types of data are associated with what types of medical devices. In this example, the computing device determines that the medical device data was generated by a medical imaging machine. The computing device may then use a machine learning model (a separate model or the same) that has learned what services are associated with what types of medical devices. In this example, the computing device uses the machine learning model to infer that the medical device data from the medical imaging machine is associated with radiology services. The computing device then generates data indicating that radiology services were performed by a health care provider.

At 204, the computing device may sanitize and/or store data indicating services that have previously been provided by one or more health care providers. For example, the computing device may remove personal data from the data obtained at 202. The computing device may store the data in a database in a sanitized or unsanitized format.

At 206, the computing device may cluster health care providers. For example, based on the data obtained at 202 and/or sanitized at 204, the computing device may cluster a plurality of health care providers according to types of services that have been provided, types of services that have recently been provided (e.g., over the last week, month, year, etc.), types of services that have been provided most frequently (e.g., a type of service that a health care provider performs the most, second most, etc.), a number of times a type of service has been provided, and so on.

At 208, the computing device may determine one or more categories associated with a cluster. For example, the computing device may determine that a cluster includes health care providers that have provided services associated with one or more categories.

At 210, the computing device may associate one or more health care providers of a cluster with one or more categories determined at 208. For example, the computing device may associate (e.g., tag, update a profile or account, etc.) health care providers that are associated with a same cluster with one or more categories that are associated with the cluster. In some examples, operations 208 and/or 210 may be referred to as categorizing health care providers.

In some examples, operations 208 and/or 210 may be repeated any number of times for any number of clusters. For example, at 208, the computing device may determine that a first cluster is associated with one or more first categories and determine that a second cluster is associated with one or more second categories. In some instances, the one or more first categories associated with the first cluster may include at least some of the one or more second categories associated with the second cluster. In other instances, the one or more first categories associated with the first cluster may be completely different than the one or more second categories associated with the second cluster. Then, at 210, the computing device may associate health care providers that are associated with the first cluster with the one or more first categories and health care providers that are associated with the second cluster with the one or more second categories.

At 212, the computing device may receive a request for data about a health care provider associated with a particular category. The request may be received from a medical service device, a user device, or any other device.

At 214, the computing device may determine one or more health care providers that are associated with the particular category. For example, the computing device may reference profiles or accounts for a plurality of health care providers to determine one or more health care providers that are associated with the particular category (e.g., have been clustered into a cluster that is associated with the particular category and categorized based on such clustering). Operation 214 may determine one or more health care providers that satisfy the request received at 212.

At 216, the computing device may determine one or more health care providers that have been designated as being associated with the particular category and that lie outside a cluster associated with the particular category.

At 218, the computing device may send information regarding the one or more health care providers that are associated with the particular category. The information may be sent to the device that requested the information (e.g., the device form which the request was received at 212). In some examples, the information may not include information regarding the one or more health care providers that have been designated as being associated with the particular category and that lie outside the cluster associated with the particular category.

FIG. 3 illustrates the example process 300 for providing information regarding a health care provider that is registering with a system (e.g., a service provider). In some examples, the process 300 is performed after a plurality of health care providers have been clustered and/or categorized (e.g., after performing the process 200 of FIG. 2). In other examples, the process 300 may be performed at other times.

At 302, a computing device may receive a request to register a health care provider. For example, the computing device may receive a request from a medical service device, user device, computing device associated with the health care provider, or other device to register a new health care provider with a service provider (e.g., a health care provider that has not yet joined/registered with the service provider, a health care provider that is changing employment to be associated with the service provider, etc.). In some examples, the request may identify a category that has been designated for the health care provider (e.g., an area of services that the health care provider believes he or she is associated with).

At 304, the computing device may receive data indicating services that have previously been provided by the health care provider. For example, the computing device may retrieve data from a previous employer of the health care provider, receive data overtime during an initial period of employment (e.g., a first few months of practicing after having registered with the service provider, etc.), and so on.

At 306, the computing device may determine that a number of services that the health care provider has performed for the category designated for the health care provider is more than or less than a threshold. For example, the computing device may have clustered a plurality of health care providers into clusters and determined categories for the clusters. The computing device may set a threshold for a cluster to an average number of services that have been performed by health care providers associated with the cluster, to a particular number more or less than the average (e.g., ten more than the average), etc. The computing device may identify a cluster that is associated with the category that is designated for the health care provider and determine if the number of services that the health care provider has performed is more or less than the threshold associated with the cluster.

At 308, the computing device may send a notification regarding the health care provider. The notification may be sent to a medical service device, a user device, a computing device associated with the health care provider, or any other device. For example, if the health care provider has performed more services of the category designated for the health care provider than a threshold associated with a cluster for the category, then the notification may indicate to associate the health care provider with the category (e.g., recommend such category). Alternatively, if the health care provider has performed less services of the category designated for the health care provider than a threshold associated with a cluster for the category, then the notification may indicate that the health care provider practices outside the category that is designated for the health care provider or may indicate to associate the health care provider with a different category.

FIG. 4 illustrates the example process 400 for analyzing a category that is designated for a health care provider. In some examples, the process 400 is performed after and/or during clustering and/or categorization of health care providers. In other examples, the process 400 may be performed at other times.

At 402, a computing device may retrieve a profile or account for a health care provider. For example, the computing device may reference a database of profiles or accounts to obtain profile or account data for the health care provider.

At 404, the computing device may determine that the health care provider has been designated as being associated with a particular category of providing medical services. For example, the computing device may determine, based on the profile or account for the health care provider, a particular category that has been designated or advertised by the health care provider.

At 406, the computing device may determine that the health care provider lies outside a cluster that is associated with the particular category. For example, the computing device may have clustered a plurality of health care providers into clusters and determine that the health care provider lies outside a first cluster that is associated with the particular category. In one example, this includes determining a type of service that is associated with the first cluster and determining that the health care provider does not perform the type of service that is associated with the first cluster. In another example, this includes determining an average number of times a service that is associated with the first cluster has been provided by health care providers associated with the first cluster, determining a threshold based on the average number of times (e.g., the threshold being the average or a particular number below or above the average), and determining that a number of times the health care provider has performed the service that is associated with the first cluster is less than the threshold.

At 408, the computing device may update the profile or account of the health care provider to indicate that the health care provider practices outside of the particular category that is designated for the health care provider. Operation 408 may be based on the determination at operation 404 and/or 406.

At 410, the computing device may send a notification indicating that the health care provider practices outside the particular category that is designated for the health care provider. The notification may be sent to a medical service device, a user device, a computing device associated with the health care provider, or any other device.

Conclusion

Although embodiments have been described in language specific to structural features and/or methodological acts, it is to be understood that the disclosure is not necessarily limited to the specific features or acts described. Rather, the specific features and acts are disclosed herein as illustrative forms of implementing the embodiments.

What is claimed is:

1. A method comprising:
receiving, by a remote computing system and from each of a plurality of computing devices associated with a plurality of health care providers, respectively, data indicating one or more services that have been provided by the health care provider associated with the respective computing device, the data including personal data about one or more patients;

sanitizing, by the remote computing system, the data of the plurality of health care providers to remove the personal data;

storing, by the remote computing system, the sanitized data of the plurality of health care providers in a database;

retrieving, by the remote computing system, the sanitized data of the plurality of health care providers from the database;

generating input data based at least in part on the retrieved data, the input data generated by:
 determining, for each of the plurality of health care providers, one or more types of services that have been provided by the respective health care provider; and
 determining, for each of the plurality of health care providers, a number of times the respective health care provider providing each of the one or more types of services;

generating a machine learning model configured to receive the input data and generate results data representing health care provider clusters that indicate actual services previously provided by the health care providers;

training the machine learning model to determine the health care provider clusters utilizing, as a training dataset, a medical device type associated with the services such that a trained machine learning model is generated;

generating, utilizing the trained machine learning model, first data indicating one or more clusters of the plurality of health care providers, the one or more clusters representing nodes in a nodal space generated via the trained machine learning model;

retrieving, by the remote computing system, a profile for a first health care provider of the plurality of health care providers;

based at least in part on the profile for the first health care provider, determining, by the remote computing system, that the first health care provider has been designated as being associated with a first category of providing medical services;

determining, by the remote computing system, that the first health care provider lies outside of a first cluster, from among the one or more clusters, that is associated with the first category;

based at least in part on determining that the first health care provider has been designated as being associated with the first category and determining that the first health care provider lies outside of the first cluster that is associated with the first category, updating, by the remote computing system, the profile to indicate that the first health care provider practices outside of the first category that is designated by the first health care provider; and sending, by the remote computing system and to a device associated with a medical service, a notification indicating that the first health care provider practices outside the first category that is has been designated as being associated with the first health care provider.

2. The method of claim 1, wherein:
 the clustering comprises clustering the plurality of health care providers according to the one or more types of services that have been provided by individual ones of the plurality of health care providers and the number of times the one or more types of services have been provided; and
 the determining that the first health care provider lies outside of the first cluster comprises determining that the first health care provider is positioned more than a threshold distance from a center of the first cluster.

3. The method of claim 1, wherein the determining that the first health care provider lies outside of the first cluster comprises:
 determining a type of service that is associated with the first cluster; and
 determining that the first health care provider does not perform the type of service that is associated with the first cluster.

4. The method of claim 1, wherein the determining that the first health care provider lies outside of the first cluster comprises:
 determining an average number of times a service that is associated with the first cluster has been provided by the health care providers associated with the first cluster;
 determining a threshold based at least in part on the average number of times; and
 determining that a number of times the first health care provider has performed the service that is associated with the first cluster is less than the threshold.

5. The method of claim 1, further comprising:
 receiving, by the remote computing system and from at least one of the device associated with the medical service or a device associated with a user, a request for information regarding health care providers that are associated with the first category; and
 sending, by the remote computing system, information indicating a health care provider, from among the plurality of health care providers, that is associated with the first cluster.

6. A system comprising:
 one or more processors; and
 memory communicatively coupled to the one or more processors and storing executable instructions that, when executed by the one or more processors, cause the one or more processors to perform operations comprising:
  obtaining first data indicating services that have previously been provided by a plurality of health care providers;
  generating input data based at least in part on the first data;
  generating a machine learning model configured to receive the input data and generate results data representing health care provider clusters that indicate actual services previously provided by the plurality of health care providers;
  training the machine learning model to determine the health care provider clusters utilizing, as a training dataset, a medical device type associated with the services such that a trained machine learning model is generated;
  generating, utilizing the trained machine learning model, second data indicating one or more clusters of the plurality of health care providers, the one or more clusters based at least in part on types of services that have been provided and a number of times the types of services have been provided and the medical device type, generating the one or more clusters including:
  clustering a first health care provider and a second health care provider of the plurality of health care providers into a first cluster based at least in part on the first health care provider and the second health care provider each having provided a first type of service, a number of times the first health care provider provided the first type of service, and a number of times the second health care provider provided the first type of service; and
  clustering a third health care provider and a fourth health care provider of the plurality of health care providers into a second cluster based at least in part on the third health care provider and the fourth health care provider each having provided a second type of service, a number of times the third health care provider provided the second type of service, and a number of times the fourth health care provider provided the second type of service, the first cluster and the second cluster representing nodes in a nodal space generated via the trained machine learning model;
  determining that the first cluster is associated with a first category;
  determining that the second cluster is associated with a second category;
  tagging the first health care provider and the second health care provider with the first category and tagging the third health care provider and the fourth health care provider with the second category;
  receiving, from at least one of a device associated with a medical service or a device associated with a user, a request for data about a health care provider associated with the first category;
  determining that the first health care provider is associated with the first category; and
  sending, to at least one of the device associated with the medical service or the device associated with the user, information regarding the first health care provider.

7. The system of claim 6, wherein the operations further comprise:
  determining that a fifth health care provider of the plurality of health care providers has been designated as being associated with the first category for an area in which the fifth health care provider practices;
  determining that the fifth health care provider lies more than a threshold distance from a center of the first cluster; and
  refraining from including information about the fifth health care provider in the information that is sent to at least one of the device associated with the medical service or the device associated with the user.

8. The system of claim 6, wherein the operations further comprise:
  receiving a request to register an additional health care provider;
  receiving data indicating services that have previously been provided by the additional health care provider;
  based at least in part on the data indicating services that have previously been provided by the additional health care provider, determining that the additional health care provider has provided more than a threshold number of services of the first type of service associated with the first category; and
  sending a recommendation to associate the additional health care provider with the first category associated with the first cluster.

9. The system of claim 6, wherein the operations further comprise:
  receiving a request to register an additional health care provider, the request indicating that the additional health care provider has been designated as being associated with the first category;
  receiving data indicating services that have previously been provided by the additional health care provider;
  based at least in part on the data indicating services that have previously been provided by the additional health care provider, determining that the additional health care provider performs less than a threshold number of services of the first type of service associated with the first category; and
  sending a notification indicating that the additional health care provider practices outside the first category that has been designated as being associated with the additional health care provider.

10. The system of claim 9, wherein the notification is sent to a device associated with the additional health care provider.

11. The system of claim 9, wherein the notification is sent to the device associated with the medical service.

12. The system of claim 6, wherein the operations further comprise:
  sanitizing the data of the plurality of health care providers to remove personal data; and
  storing the sanitized data of the plurality of health care providers in a database.

13. The system of claim 6, wherein the obtaining the data indicating services that have previously been provided by the plurality of health care providers comprises:
  automatically receiving medical device data from one or more medical devices when the one or more medical devices generate the medical device data; and
  analyzing the medical device data to determine types of medical devices that generated the medical device data; and
  generating the input data based at least in part on the types of the medical devices.

14. One or more non-transitory computer readable media storing executable instructions that, when executed by one or more processors, cause the one or more processors to perform operations comprising:
  obtaining first data indicating services that have previously been performed by a plurality of health care providers;
  generating input data based at least in part on the first data;
  generating a machine learning model configured to receive the input data and generate results data representing health care provider clusters that indicate actual services previously provided by the plurality of health care providers;
  training the machine learning model to determine the health care provider clusters utilizing, as a training dataset, a medical device type associated with the services such that a trained machine learning model is generated;
  generating, utilizing the trained machine learning model, second data indicating one or more clusters of the plurality of health care providers, the one or more clusters based at least in part on types of services that have previously been performed by the plurality of health care providers and a number of times the types of services have previously been performed by the plurality of health care providers, the one or more clusters representing nodes in a nodal space generated via the trained machine learning model;

categorizing a first health care provider, from among the plurality of health care providers, that is associated with a first cluster, from among the plurality of clusters;

receiving, from at least one of a device associated with a medical service or a device associated with a user, a request for data about a health care provider;

determining that the first health care provider satisfies the request based at least in part on the categorizing of the first health care provider; and sending, to at least one of the device associated with the medical service or the device associated with the user, information regarding the first health care provider.

15. The one or more non-transitory computer-readable media of claim 14, wherein the operations further comprise:
  receiving a request to register an additional health care provider;
  receiving data indicating services that have previously been performed by the additional health care provider;
  based at least in part on the data indicating services that have previously been performed by the additional health care provider, categorizing the additional health care provider into a same category as the first health care provider; and
  sending a recommendation to associate the additional health care provider with the category associated with the first health care provider.

16. The one or more non-transitory computer-readable media of claim 14, wherein the operations further comprise:
  receiving a request to register an additional health care provider, the request indicating that the additional health care provider has been designated as being associated with a category;
  receiving data indicating services that have previously been performed by the additional health care provider;
  based at least in part on the data indicating services that have previously been performed by the additional health care provider and the categorizing, determining that the additional health care provider performs less than a threshold number of services that are associated with the category; and
  sending a notification indicating that the additional health care provider practices outside the category that has been designated as being associated with the additional health care provider.

17. The one or more non-transitory computer-readable media of claim 16, wherein the notification is sent to a device associated with the additional health care provider.

18. The one or more non-transitory computer-readable media of claim 16, wherein the notification is sent to the device associated with the medical service.

19. The one or more non-transitory computer-readable media of claim 14, wherein the operations further comprise:
  sanitizing the data of the plurality of health care providers to remove personal data; and
  storing the sanitized data of the plurality of health care providers in a database.

20. The one or more non-transitory computer-readable media of claim 14, wherein the obtaining the data indicating services that have previously been performed by the plurality of health care providers comprises:
  automatically receiving medical device data from one or more medical devices when the one or more medical devices generate the medical device data;
  analyzing the medical device data to determine types of medical devices that generated the medical device data; and
  generating the input data based at least in part on the types of the medical devices.

\* \* \* \* \*